(12) United States Patent
Shinjo et al.

(10) Patent No.: US 7,601,153 B2
(45) Date of Patent: Oct. 13, 2009

(54) INTRAMEDULLARY NAIL

(75) Inventors: Akira Shinjo, Chino (JP); Kijyuro Hayano, Chino (JP)

(73) Assignee: Homs Engineering Inc., Chino-Shi, Nagano (JP)

( * ) Notice: Subject to any disclaimer, the term of this patent is extended or adjusted under 35 U.S.C. 154(b) by 1013 days.

(21) Appl. No.: 11/018,962

(22) Filed: Dec. 21, 2004

(65) Prior Publication Data
US 2005/0143739 A1 Jun. 30, 2005

(30) Foreign Application Priority Data
Dec. 25, 2003 (JP) ............................. 2003-429252

(51) Int. Cl.
*A61B 17/56* (2006.01)
*A61B 17/58* (2006.01)
*A61F 2/30* (2006.01)

(52) U.S. Cl. .......................................... 606/64; 606/62

(58) Field of Classification Search ............. 606/62–68, 606/313, 326–329; 623/23.23, 23.26, 23.27; 403/109.5, 184, 350
See application file for complete search history.

(56) References Cited

U.S. PATENT DOCUMENTS

| 6,835,197 B2 * | 12/2004 | Roth et al. ..................... 606/62 |
| 2005/0069397 A1 * | 3/2005 | Shavit et al. ................. 411/457 |
| 2005/0090821 A1 * | 4/2005 | Berrevoets et al. ............. 606/61 |

FOREIGN PATENT DOCUMENTS

| EP | 1 175 872 A2 | 1/2002 |
| JP | A-H02-21859 | 1/1990 |
| JP | PAJ02/021859 | 1/1990 |
| JP | A-H11-137566 | 5/1999 |
| JP | PAJ11-137566 | 5/1999 |
| JP | A-2000-342596 | 12/2000 |
| JP | PAJ2000-342596 | 12/2000 |
| JP | A-2002-35000 | 2/2002 |
| JP | PAJ2002-035000 | 2/2002 |
| JP | A-2003-533242 | 11/2003 |
| JP | 2004-372754 | 12/2004 |
| WO | WO 01/52758 A1 | 7/2001 |
| WO | WO 02/098330 A2 | 12/2002 |
| WO | WO 03/061495 A2 | 7/2003 |
| WO | WO 03/094763 A1 | 11/2003 |

OTHER PUBLICATIONS

EO 04 25 8039 Partial European Search Report.
International Search Report, PCT/EP 02/05235, Jan. 10, 2003.
European Search Report, EP 04 25 8039, Dec. 21, 2005.

* cited by examiner

*Primary Examiner*—Thomas C Barrett
*Assistant Examiner*—Andrew Yang

(57) ABSTRACT

The present invention is an intramedullary nail (100) to be used by being intramedullarily inserted into a bone, having a nail body (110) comprising an axial hole (113) extending from an opening formed at a proximal end portion toward a distal end portion along an axis line and a transverse hole (114) intersecting with the axis line, and having: an engaging member (221) comprising an engaging portion (221b) at distal end thereof engageable with a bone fastener inserted through the transverse hole and arranged so as to be shiftable in the axial hole in a manner where the distal end portion is engageable and disengageable with the bone fastener (10); an adjusting member (222) controlling the position of the engaging member; and an elastic member (125) for charging, against the nail body, the engaging member in a direction opposite the controlling direction by the adjusting member.

5 Claims, 6 Drawing Sheets

FIG. 3
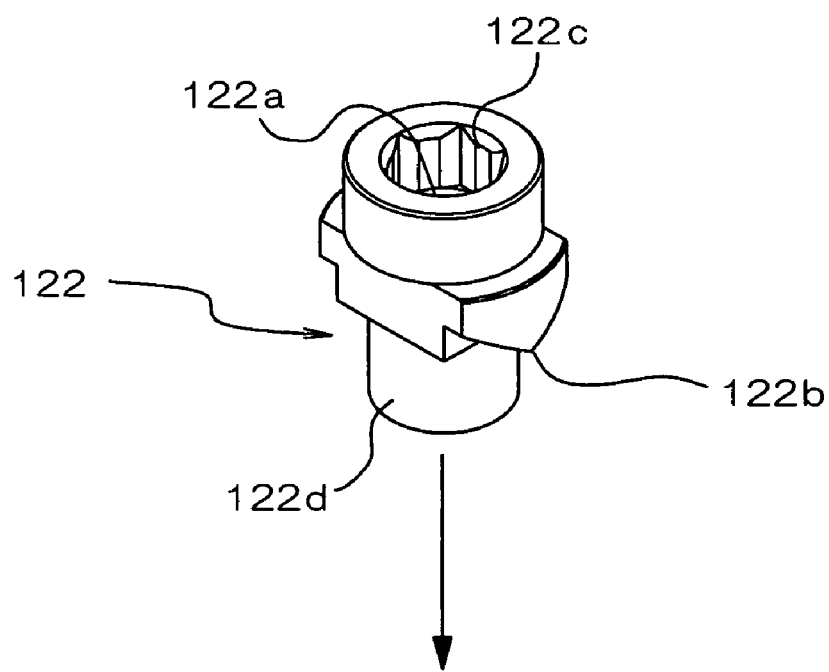
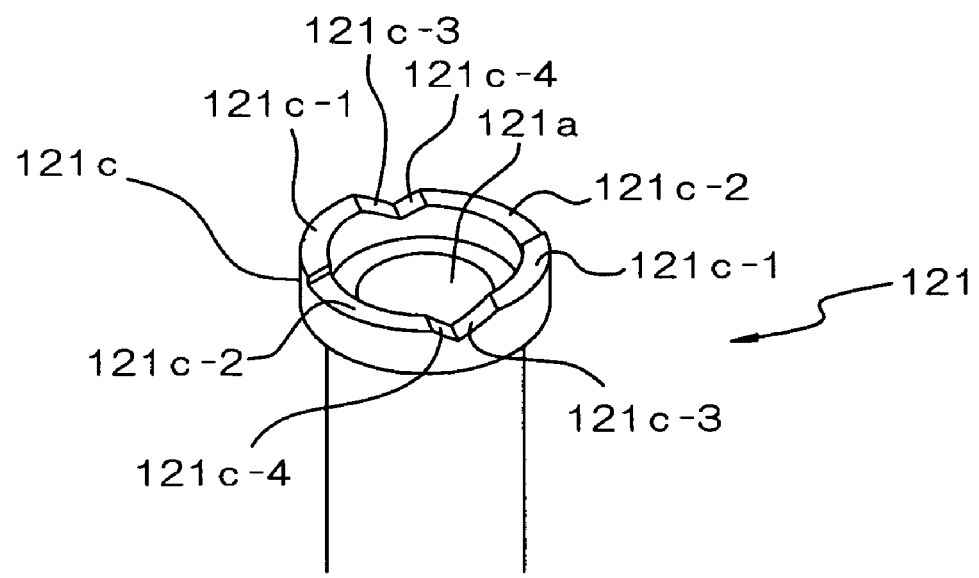

(a)

(b)

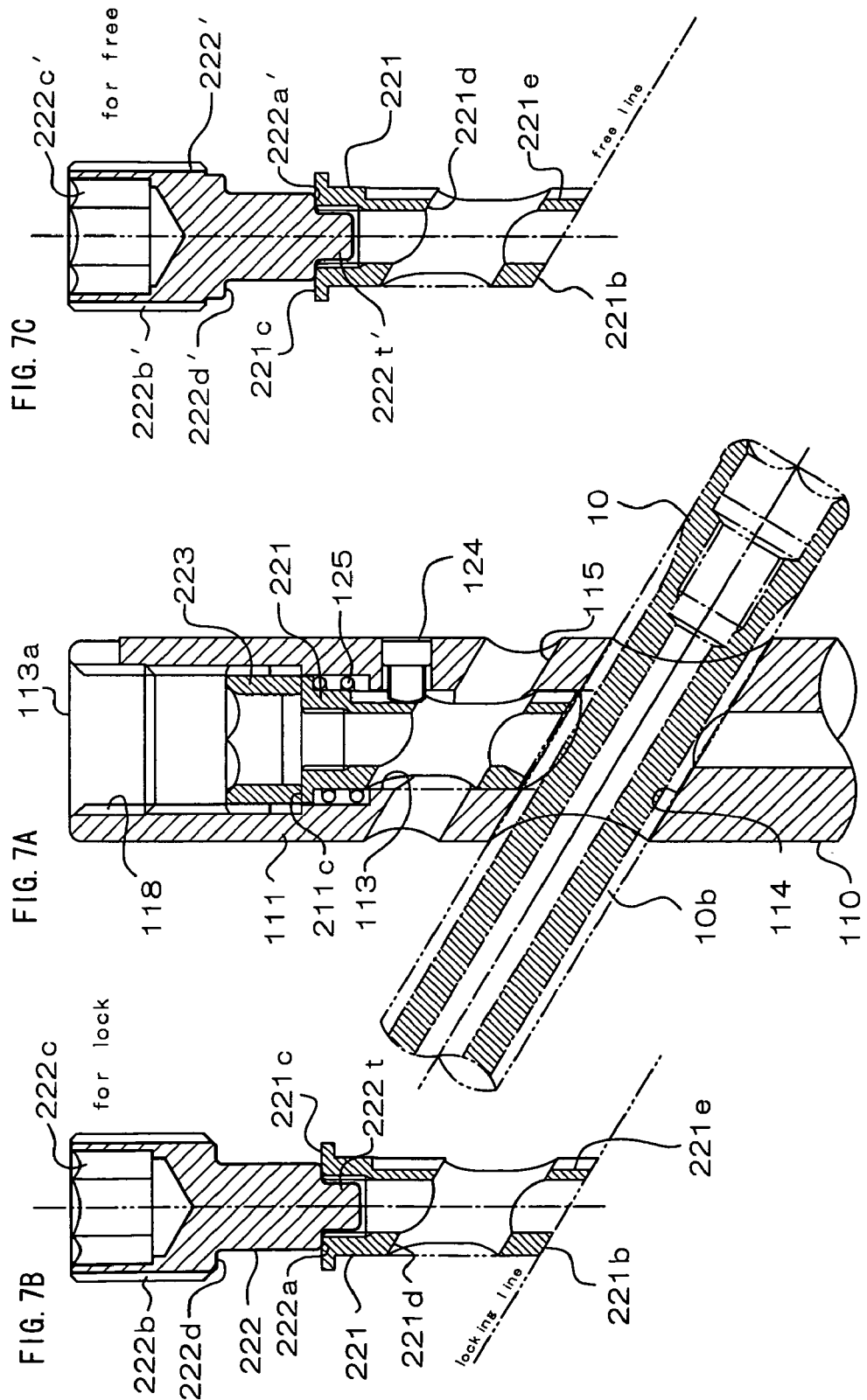

slide free  slide lock

INTRAMEDULLARY NAIL

CROSS-REFERENCE TO RELATED PATENT APPLICATION

This patent application claims priority on Japanese Patent Application No. 2003-429252 filed on Dec. 25, 2003. The entire disclosure of this Japanese Patent Application, including the specification, claims, drawings and summary, are also incorporated herein by reference.

FIELD OF THE FIELD

The present invention relates to an intramedullary nail, and in particular, it relates to a structure of an intramedullary nail preferred for a fracture treatment of an upper portion of a femur.

BACKGROUND OF THE INVENTION

Generally, as osteosynthesis means for treating fractures of upper portions of femurs, intramedullary nails comprising a nail body to be intramedullarily inserted from proximal parts of femurs have been used. These intramedullary nails include, for example, one as described in the specification of European Patent Publication NO. 0257118. This has an axial hole extending from an opening provided at a proximal end portion toward a distal end portion in an axis direction and a transverse hole formed in a direction intersecting with the axis direction, and by inserting a bone fastener (bone screw) through this transverse hole and inserting and fixing its distal end inside the bone, a bone fracture is prevented or a rotation of the intramedullary nail is prevented.

In this type of intramedullary nail, by screwing an adjusting screw (set screw) into the axial hole through the opening provided in its proximal end portion, the distal end of this adjusting screw is engaged with the outer circumferential surface of the bone fastener inserted through the transverse hole, whereby the bone fastener is prevented from rotating with respect to the nail body or is completely fixed.

On the other hand, when the above-described intramedullary nail is used in a case where a fracture line exists between the femoral bone head portion and tubular portion, there is a danger that at the end of the femur, the bone head portion may be rotated around the axis line of the bone fastener inserted in the bone head portion. For prevention thereof, as described in, for example, U.S. Pat. No. 5,531,748, in some cases, a plurality of transverse holes are provided in the nail body, and a plurality of bone fasteners respectively inserted through these transverse holes are inserted into the bone head portion.

However, in the aforementioned intramedullary nail, although it is necessary to screw the adjusting screw into the axial hole of the nail body and engage its distal end with the bone fastener after inserting the bone fastener through the transverse hole of the nail body and screwing the same toward the inside of the femur, since the engaged condition with the bone fastener is adjusted by a screwing amount of the adjusting screw, the degree of adjustment is difficult, therein a problem has existed.

In greater detail, in most cases, on the outer circumferential surface of the bone fastener, an engaging groove extending in its axis direction has been formed. And, by engaging the distal end of the adjusting screw with this engaging groove, the bone fastener can be brought into a condition (slide-free condition) where the bone fastener is, with respect to the nail body, slidable in its axis direction but cannot rotate around its axis line, and in addition, by strongly bringing the distal end of the adjusting screw into contact against the bottom surface of the engaging groove, the bone fastener can also be brought into a condition (slide-lock condition) where the bone fastener has been completely (including in its axis direction) fixed to the nail body.

Nevertheless, generally, since the bone fastener is often provided in the slide-free condition with respect to the nail body, it is necessary to subtly adjust the screwing amount of the adjusting screw in order to obtain this slide-free condition. For example, on a surgical site, normally, subtle operations such as returning the adjusting screw by a predetermined amount from a position where the adjusting screw has been completely screwed so that the bone fastener reaches the slide-lock condition have been performed, and it is impossible to completely deny a risk of the fastener reaching the slide-lock condition or the fastener reaching a perfectly free condition (being rotatable around the axis line thereof) to the contrary if this delicate operation is mishandled. In addition, there is also a problem such that, since the adjusting screw has been merely screwed into the nail body, the adjusting screw is not sometimes correctly determined owing to a looseness of this screwed structure, this encourages failure of the operation, and operation resistance increases if the looseness of the screwed structure is reduced, therefore the operation becomes difficult.

Furthermore, in the case where a plurality of transverse holes are formed in a nail body and two or more bone fasteners are inserted (screwed) into a femoral bone head portion, there is a problem such that, bone fasteners inserted through transverse holes formed on the proximal end side of the nail body can be engaged and retained by the adjusting screw inserted through an opening provided at a proximal end portion of the nail body, whereas for bone fasteners inserted through the side of a distal end portion, the adjusting screw cannot be engaged therewith by being obstructed by the bone fasteners inserted through the proximal end portion side.

SUMMARY OF THE INVENTION

Therefore, the present invention has been made to solve the above-described problems, and it is an object thereof to provide an engaging structure that can engage a bone fastener, which is inserted through a transverse hole provided in a nail body, easily and securely or accurately with respect to the nail body.

In order to solve the problems as described above, an intramedullary nail according to a first aspect of the invention is an intramedullary nail to be used by being intramedullarily inserted into a bone, having a nail body comprising an axial hole extending from an opening formed at a proximal end portion toward a distal end portion along an axis line and a transverse hole intersecting with the axis line, and it has an engaging member comprising an engaging portion engageable with a bone fastener inserted through the transverse hole and arranged so as to be shiftable in the axial hole in a manner where the engaging portion is engageable and disengageable with the bone fastener, and an adjusting member for adjusting the position of the engaging member.

In particular, the adjusting means of the present invention is characterized in being provided so that a rotating operation is possible and having a cam engagement with the engaging member so as to change a controlling position for the engaging member according to its rotation angle in a condition substantially fixed in an axis direction.

According to the first aspect of the invention, since the adjusting member is, when being operated to rotate, changed in the controlling position for the engaging member in a condition substantially fixed in the axis direction, by appropriately setting the structure of a cam engagement, a desirable engaging condition for a bone fastener can be securely obtained without being affected by a subtle change in the operating amount, therefore such a necessity, as in the background art, of subtly adjusting the screwing amount in order to accurately set the position in the axis direction of adjusting screw is eliminated. In addition, since the operating amount for the adjusting member can also be reduced without lowering the operating accuracy by the structure of the cam engagement, it becomes possible to improve operationality. Accordingly, it becomes possible to set an engaging condition of the engaging member for the bone fastener inserted through the transverse hole easily and securely or accurately.

In addition, an intramedullary nail according to a second aspect of the invention is an intramedullary nail to be used by being intramedullarily inserted into a bone, having a nail body comprising an axial hole extending from an opening formed at a proximal end portion toward a distal end portion along an axis line and a transverse hole intersecting with the axis line, and is characterized in having: an engaging member comprising an engaging portion at distal end thereof engageable with a bone fastener inserted through the transverse hole and arranged so as to be shiftable in the axial hole in a manner where the engaging portion is engageable and disengageable with the bone fastener; an adjusting member controlling the position of the engaging member; and an elastic member for charging, against the nail body, the engaging member in a direction opposite the controlling direction by the adjusting member.

According to the second aspect of the invention, by controlling the engaging member to engage and retain a bone fastener from one side by use of the adjusting member and also charging the same from the other side by use of the elastic member, the position of the engaging member can be correctly adjusted by the simple construction. In addition, since the engaging member can be prevented from being projected from the transverse hole by a charge of the elastic member, the bone fastener can be easily inserted into the transverse hole and engagement between the bone fastener and engaging member can also be prevented. Accordingly, an engaging condition of the engaging member for the bone fastener can be set easily and securely or accurately.

BRIEF DESCRIPTION OF THE DRAWINGS

FIG. 3 is an exploded perspective view of an engaging member and an adjusting member of the same embodiment, FIG. 7A is an enlarged sectional view of a proximal region of an intramedullary nail of further different embodiment, FIG. 7B is an enlarged sectional view of an engaging condition between an engaging member and an adjusting member, FIG. 7C is an enlarged sectional view of an engaging condition between the engaging member and an adjusting member with different length.

DETAILED DESCRIPTION OF THE PREFERRED EMBODIMENTS

Figure 1:
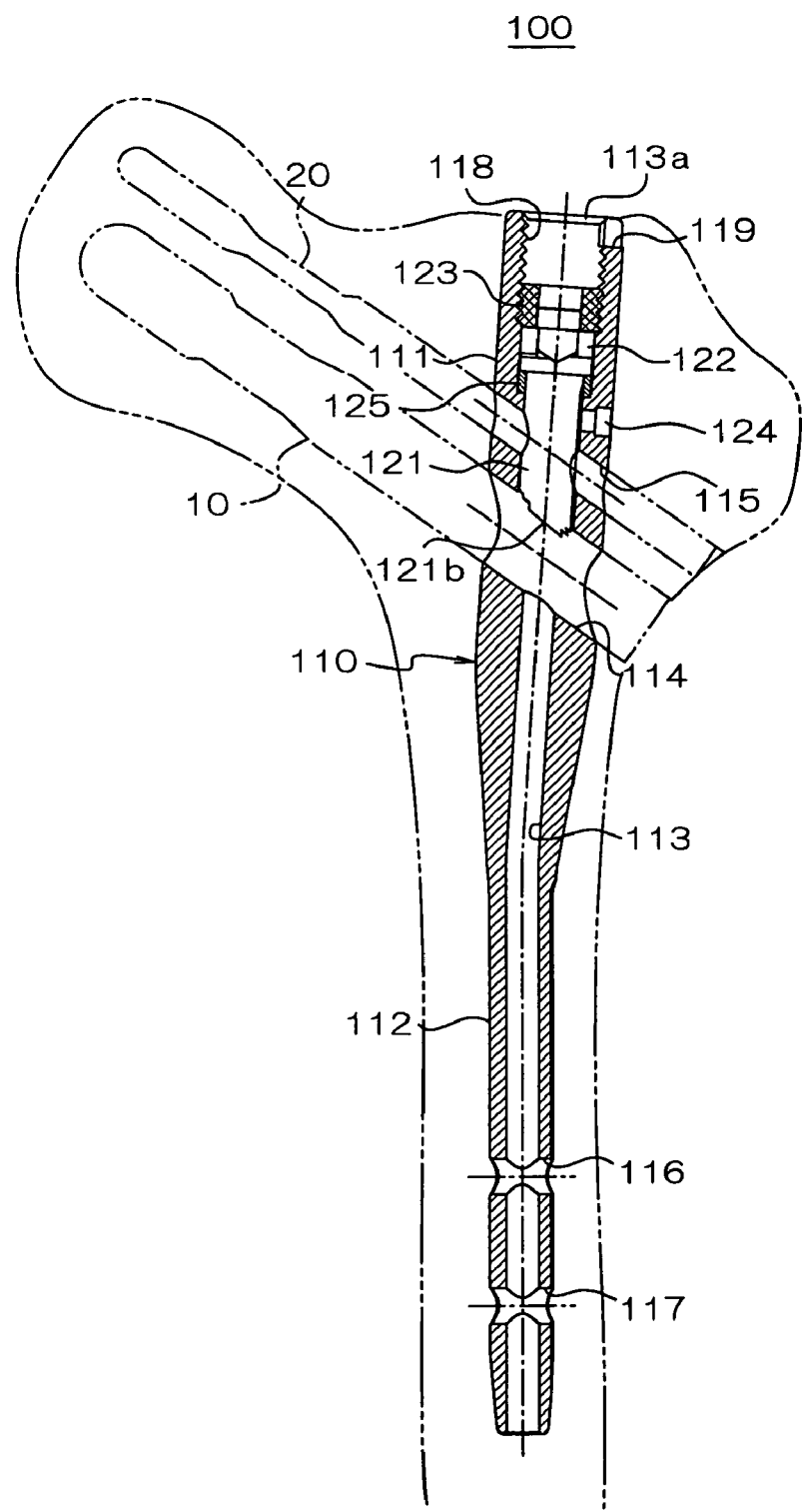
FIG. 1 is a schematic longitudinal sectional view showing an overall construction of an embodiment of an intramedullary nail according to the present invention.
Figure 2:
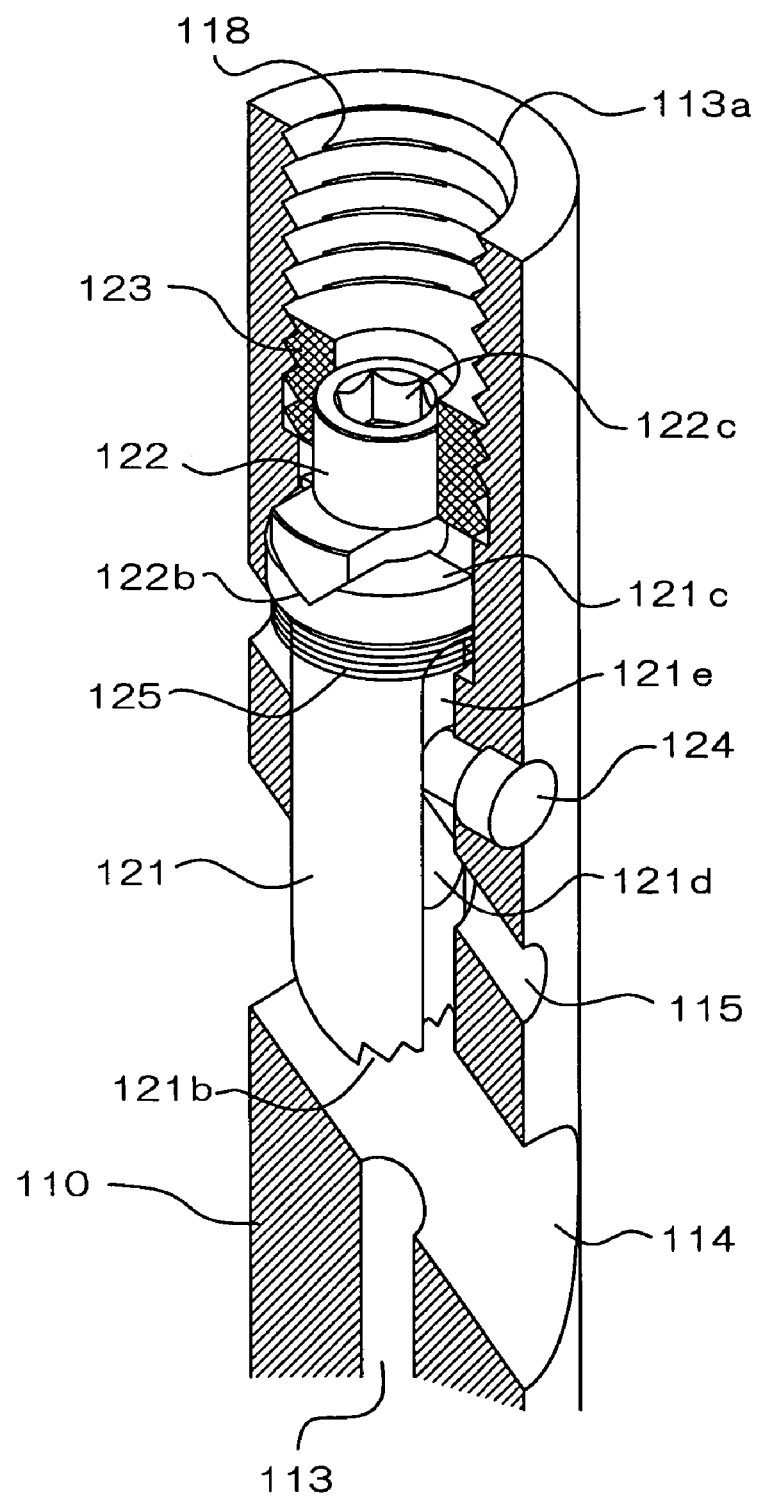
FIG. 2 is an enlarged partial longitudinal section perspective view of the same embodiment.

Hereinafter, an embodiment of the present invention will be described along with an illustrated example. FIG. 1 is a longitudinal sectional view showing an overall construction of an intramedullary nail 100 of the present embodiment, and FIG. 2 is an enlarged partial longitudinal section perspective view showing a longitudinal section of a proximal region of the intramedullary nail 100 in an enlarged manner. This intramedullary nail 100 has a nail body 110 extending axially from a proximal end portion to a distal end portion. This nail body 110 is preferably composed of a biocompatible material such as, for example, titanium, titanium alloy, a biodegradable resin and the like. The nail body 110 has a proximal region 111 provided at its proximal end side and a distal region 112 connected to the proximal region. The proximal region 111 preferably has a diameter larger than that of the distal region 112, and the proximal region 111 and the distal region 112 preferably have axis lines with a slight angular difference from each other.

In the nail body 110, an axial hole 113 having an opening 113a provided at its proximal end portion and extending from this opening 113a toward its distal end in the axis direction is provided. This axial hole 113 is not necessarily extended to a distal end portion, but is desirably, as in the illustrated example, a through-hole reaching a distal end portion. Also, in the nail body 110, transverse holes 114 and 115 constructed so as to intersect with its axis line are provided. In the present embodiment, a plurality of (in the illustrated example, two) transverse holes 114 and 115 are respectively disposed in the axis direction. The transverse holes 114 and 115 are provided so as to penetrate through the nail body 110 obliquely upward when, as in the illustrated example, the nail body 110 is brought into such a posture that the axis line becomes almost vertical. The direction of these transverse holes 114 and 115 coincides with a direction toward a femoral bone head portion when the intramedullary nail 100 is arranged inside a marrow at the proximal part side of a femur.

Inside the axial hole 113 of the nail body 110, an engaging member 121 is arranged. This engaging member 121 is arranged at a position where its distal-end engaging portion (corresponding to the above engaging portion in the present invention) 121b faces the inside of the transverse hole 114. Concretely, the engaging member 121 is arranged in a manner extending from a proximal-end-portion side further than the transverse hole 115 formed on a proximal-end-portion side, across this transverse hole 115, further to a range facing the transverse hole 114.

Figure 4A:
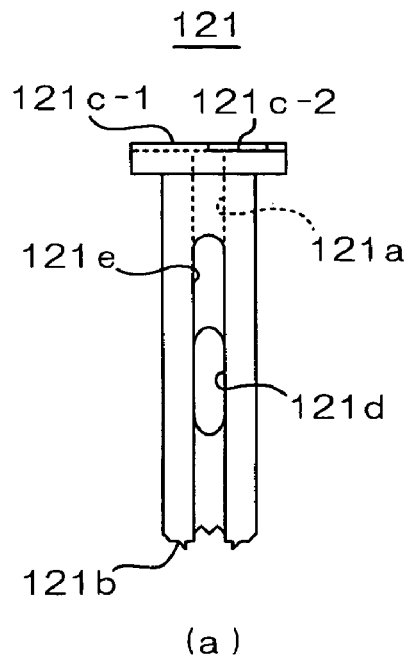
FIG. 4A is a front view of an engaging member of the same embodiment.
Figure 4B:
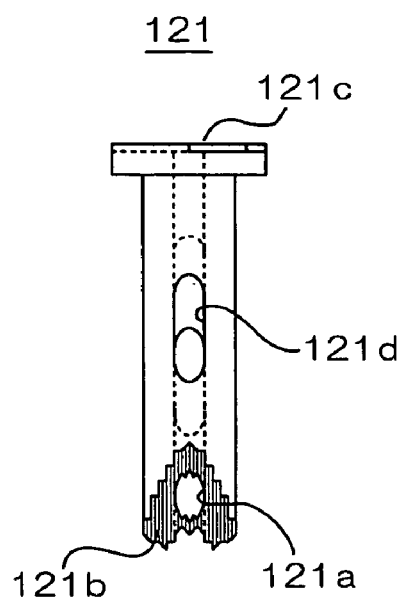
FIG. 4B is a rear view of an engaging member of the same embodiment.

FIG. 4A is a front view of the engaging member 121, and FIG. 4B is a rear view of the engaging member 121. As shown in FIG. 4, an axial hole 121a penetrating up and down is formed in the engaging member 121. This axial hole 121a is, for such a case where a method of introducing the nail body 110 into the marrow by use of a guide pin (guide wire) is employed, for allowing the guide pin or the like to pass therethrough. In addition, a distal-end engaging portion 121b of the engaging member 121 has an engaging surface comprising a schematic surface form along the inner surface of the transverse hole 114 (curved along the inner surface) and having an uneven structure in the curving direction of this schematic surface form. Namely, the engaging surface of the distal-end engaging portion 121b has a schematic surface form which is, when being made coincident with the inner surface of the transverse hole 114, fitted with an opening part by the axial hole 113 provided in this inner surface and which can construct a hypothetical inner surface part continued and coordinated with the circumference of this opening part, and on the surface of this schematic surface form, the above-described uneven structure having a predetermined uneven depth is formed. Thereby, when the engaging member 121 has been retracted upward, even if the shifting amount of retraction is slight, it is possible to easily insert a bone fastener (bone screw) such as a lag screw through the transverse hole 114, and it also becomes possible to extract the inserted bone fastener without resistance. Furthermore, when the engaging member 121 is shifted downward to project the distal-end engaging portion 121b into the transverse hole 114, an advantage is provided such that this can be securely engaged across a large area with the outer circumferential surface of the bone fastener inserted through the transverse hole 114. Here, the uneven structure provided on the engaging surface is engaged with an unillustrated uneven structure formed on the outer circumference of a bone fastener 10 shown in FIG. 1 so that the bone fastener 10 can be prevented from rotating around the axis line.

Furthermore, cam engaging surfaces 121c-1 to 121c-4 are formed on a cam engaging portion (proximal end portion) 121c of the engaging member 121. These cam engaging surfaces are constructed so as to extend in a circumferential form coaxial with a rotation axis of an adjusting member 122 (namely, in the rotating direction), which will be described later. As shown in FIG. 3, on the proximal end engaging portion 121c, provided are: the cam engaging surface 121c-1, which is formed at the most proximal-end-portion side (namely, the highest) as viewed in the axis direction; the cam engaging surface 121c-2, which is formed closer to the distal-end-portion side of the nail body 110 (namely, lower) than this cam engaging surface 121c-1; the cam engaging surface 121c-3, which is connected to this cam engaging surface 121c-1 and is inclined so as to shift to the distal-end-portion side of the nail body 110 as it becomes distant from this cam engaging surface 121c-1 along the rotating direction; and the cam engaging surface 121c-4, which is connected to the cam engaging surface 121c-2, is inclined so as to shift to the distal-end-portion side of the nail body 110 as it becomes distant from this cam engaging surface 121c-2 along the rotating direction, and is connected to the cam engaging surface 121c-3. In this cam engaging portion 121c, a connecting part between the cam engaging surfaces 121c-3 and 121c-4 is constructed at the most distal-end side of the nail body 110 (namely, the lowest.)

In addition, in the engaging member 121, a transverse opening portion 121d is formed between the distal-end engaging portion 121b and the cam engaging portion 121c. This transverse opening portion 121d is formed at a position corresponding to the transverse hole 115 formed in the nail body 110 so that an unillustrated bone fastener can be inserted through the transverse hole 115 with no difficulty. In the illustrated example, the transverse opening portion 121d comprises an opening form extending parallel to the axis line of the transverse hole 115 and slightly elongated in the up-and-down direction. Namely, this transverse opening portion 121d is constructed so as to cause no difficulty in inserting the bone fastener 20 shown in FIG. 1 even if the engaging member 121 is shifted up-and-down to some degree.

On the engaging member 121, a concave groove 121e extending in the axis direction is formed, and this concave groove 121e is engaged with a stopper member 124 (which will be described later) so that the engaging member 121 is shiftable in the axis direction but is, in the axial hole 121, not rotated around the axis line. Here, in place of this concave groove 121e, another appropriate method such as providing the engaging member 121 in a form having a noncircular transverse section may be employed so that the engaging member 121 is not rotated in the axial hole 113 of the nail body 110.

Inside the axial hole 113, for the engaging member 121, the adjusting member 122 is arranged on the proximal-end-portion side of the nail body 110. This adjusting member 122 comprises, as shown in FIG. 3, an axial hole 122a at its center. In addition, the adjusting member 122 has a cam engaging portion 122b for cam engagement with the cam engaging portion 121c of the engaging member 121. This cam engaging portion 122b is brought into contact against any of the cam engaging surfaces 121c-1 to 121c-4 and thereby controls a position in the axis direction of the engaging member 121. In addition, at a distal-end-portion side further than the cam engaging portion 122b of the adjusting member 122, a guide portion 122d which is freely rotatably fitted with the axial hole 121a of the engaging member 121a or an enlarged diametrical hole portion of the vicinity of the opening rim is provided. This fitting structure between the guide portion 122d and the axial hole 121a or enlarged diametrical hole portion has a function to guide both mutually so that the adjusting member 122 rotates concentrically with the engaging member 121.

At a proximal end portion of the adjusting member 122, an engaging structure 122c to rotate the adjusting member 122 by engaging with a tool or the like is constructed. Although this engaging structure 122c is composed of a concave hole having an angular cross section in the illustrated example, any structure may be employed as long as it can operate the adjusting member 122 to rotate.

This adjusting member 122 is retained so as not to shift to the proximal-end-portion side by a retaining member 123 arranged on the proximal-end-portion side of the nail body 110. This retaining member 123 is, in a condition screwed to a female screw 118 formed in a predetermined range from the proximal end portion toward the distal end portion of the nail body 110, engaged with a shoulder portion of the adjusting member 122. Thereby, the adjusting member 122 is, in a condition sandwiched by the engaging member 121 arranged on the distal-end-portion side of the nail body 110 and retaining member 123, rotatably arranged in the axial hole 113. In the retaining member 123, an aperture penetrated through in the axial direction is provided at the central thereof. Through this aperture, a sort of tool etc. can be inserted into the engaging structure 122c of the adjusting member. Here, the female screw 118 can also be used when an unillustrated plug for blocking the opening 113a at the proximal end portion of the nail body 110 is attached or when the nail body 110 is connected to an unillustrated fixture (a target device).

A cave hole is formed on the sidewall of the nail body 110, and inside this cave hole, the stopper member 124 is fixed by pressing or the like. The inner end of the stopper member 124 is fitted with the concave groove 121e of the engaging member 121 and thereby permits a shift in the axis direction of the engaging member 121 but prohibits a rotation around the axis line of the engaging member 121. In addition, between an outer circumferential step provided at the outer circumference of the engaging member 121 and an inner step provided inside the axial hole 113 of the nail body 110, an elastic member 125 is arranged. This elastic member 125 charges the engaging member 121 to the proximal-end-portion side in the axis direction against the nail body 110. By elastic force of this elastic member 125, the engaging member 121 is at all times pressed in contact with the adjusting member 122. This elastic member 125 can be composed of various springs such as a coil spring, a disc spring, and a torsion spring, various elastic materials such as synthetic rubber and elastic resin and the like.

In the intramedullary nail 100 of the present embodiment as described in the above, by inserting a tool or the like through the opening 113a of the proximal end portion of the nail body 110 and rotating the adjusting member 122, while the position in the axis direction of the adjusting member 122 has been substantially fixed, an engaging position between the cam engaging portion 122b of the adjusting member 122 and cam engaging portion 121c of the engaging member 121 is changed, therefore, the engaging member 121 is shifted in the axis direction of the nail body 110 while receiving an elastic force of the elastic member 121.

For example, when the cam engaging portion 122b of the adjusting member 122 has been brought in contact with the connecting part between the cam engaging surfaces 121c-3 and 121c-4, since the engaging member 121 is arranged at the most proximal-end-portion side of the nail body 110, the distal-end engaging portion 121b of the engaging member 121 does not engage (perfectly free condition) with the bone fastener 10 (see FIG. 1) inserted through the transverse hole 114. However, when the adjusting member 122 is rotated (rotated clockwise in the illustrated example) and the cam engaging portion 122b is brought into contact against the cam engaging surface 121c-2, the engaging member 121 is shifted to the distal-end-portion side of the nail body 110 and its distal-end engaging portion 121c is projected inside the transverse hole 114, therefore, an engagement with the outer circumferential surface of the bone fastener 10 makes it possible to prohibit the bone fastener 10 from rotating around its axis line (slide-free condition).

In addition, by rotating the adjusting member 122 in an reverse direction to the above (counterclockwise in the illustrated example) to bring the cam engaging portion 122b into contact against the cam engaging surface 121c-1, it becomes possible to shift the engaging member 121 to a further distal-end-portion side of the nail body 110 than the above-described slide-free condition. Thereby, since the projected amount of the distal-end engaging portion 121b into the transverse hole 114 is further increased, the bone fastener 10 can be completely fixed and also be prohibited from shifting in the axis direction (namely, slide-lock condition.)

The present embodiment described in the above provides the following effects.

Realization of an easy and secure or accurate engaging condition of the engaging member with the bone fastener: in positional adjustment of an adjusting screw as in the background art, since the position is continuously and uniformly changed by rotating the adjusting screw, subtle positional adjustment of the adjusting screw with respect to the bone fastener has been difficult, however, in the present embodiment, owing to the cam engagement between the adjusting member and engaging member, since a relationship between the operating manner to the adjusting member and position of the engaging member can be appropriately set, subtle positional adjustment also becomes easy. In particular, with an adjusting screw, looseness in the screw engagement cannot be avoided, and an attempt to eliminate this looseness increases operation resistance and deteriorates operationality, whereas in the present embodiment, the operationality is considerably improved, such that while positional accuracy of the engaging member is secured by the structure of the cam engagement, an increase in the operation resistance can be avoided, and furthermore, the operation amount (rotation amount) is also reduced.

Realization of the engaging member applicable to a plurality of bone fasteners. In the present embodiment, since the engaging member whose position is adjusted by the adjusting member as described above is engaged with the bone fastener 10, the engaging member can be fixed in the rotating direction, and as a result, by providing a transverse opening portion in the engaging member, it becomes possible to insert another bone fastener 20 therethrough.

Figure 5:
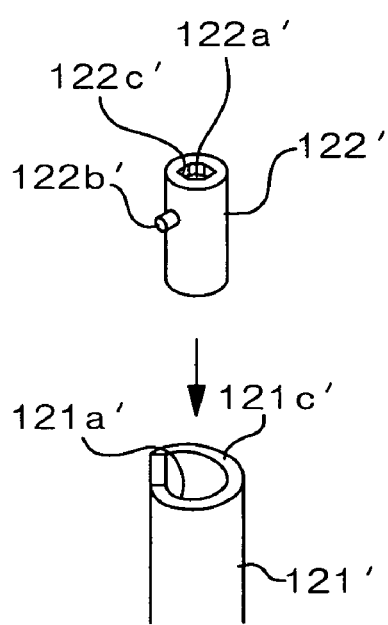
FIG. 5 is an exploded perspective view of an engaging member and an adjusting member of a different constructional example.

FIG. 5 is a schematic perspective view schematically showing a constructional example of an engaging member 121' and an adjusting member 122', which are different from those of the above-described embodiment. In this constructional example, a cam engaging portion 121c' composed of a helicoidal cam engaging surface is formed (at a proximal end portion of) in the engaging member 121', and a cam engaging portion 122b' is provided in the adjusting member 122'. In addition, in the engaging member 121', an axial hole 121a' which can store a distal end portion of the adjusting member 122' so as to be freely rotatable is provided. Furthermore, at a proximal end portion of the adjusting member 122', an engaging structure 122c' for a rotating operation is provided.

In this constructional example, similar to the above-described embodiment, by operating the adjusting member 122' to rotate after bringing the same into a condition substantially fixed in the axis direction to an unillustrated nail body, a controlling position for the engaging member 121' can be shifted in the axis direction by the cam engagement. However, since the cam engaging portion 121c' is helocoidally smoothly inclined, it is necessary to provide a construction so that the engaging member 121' is brought into a desirable engaged condition with an unillustrated bone fastener when the cam engaging portion 122b' hits thereagainst, and the condition is preferable in a case where merely realizing this engaged condition is sufficient. In order to realize a plurality of engaged conditions, a step portion or a groove portion which can retain a contact position of the cam engaging portion 122b' may be provided on the cam engaging portion 121c'.

As shown in the above-described respective embodiments, it is preferable that an angle regulating means for regulating a rotation angle of the adjusting member is provided. As this angle regulating means, a stop portion (such as a stopper or an angle contact) for stopping the rotation angle of the adjusting member at a predetermined angle or a retaining structure (such as a step or a concave groove) for retaining, at a predetermined angle, by an appropriate retaining force can be mentioned. Thereby, since it becomes possible to strictly set a rotation angle of the adjusting member by an operational feeling of an operator, the risk of operational errors can further be reduced.

In addition, it is preferable that the adjusting means is arranged, in the axial hole, at a side of the proximal end portion with respect to the engaging member and controls the position of the engaging member from the side of the proximal end portion. Thereby, since the adjusting member is arranged at the proximal-end-portion side with respect to the engaging member, the adjusting member can be directly and easily operated from the proximal-end-portion side of the nail body, thus the interior structure of the nail body can be simplified. For example, although it is possible to juxtapose the adjusting member with the engaging member when viewed in the axis direction of the nail body or to arrange the same at the distal-end-portion side of the nail body with respect to the engaging member, in this case, a direct operation to the adjusting means becomes difficult or a need to provide a structure of operating the adjusting member via a link mechanism or the like arises, thus the inner structure is complicated.

Furthermore, it is preferable to have an elastic member for charging, against the nail body, the engaging member in a direction opposite the controlling direction by the adjusting member. Thereby, since the elastic member charges the engaging member in a direction opposite the controlling direction by the adjusting member, the position of the engaging member is securely determined by a controlling condition of the adjusting member at all times, therefore, it becomes possible to adjust the position of the engaging member more easily and securely.

Figure 6:
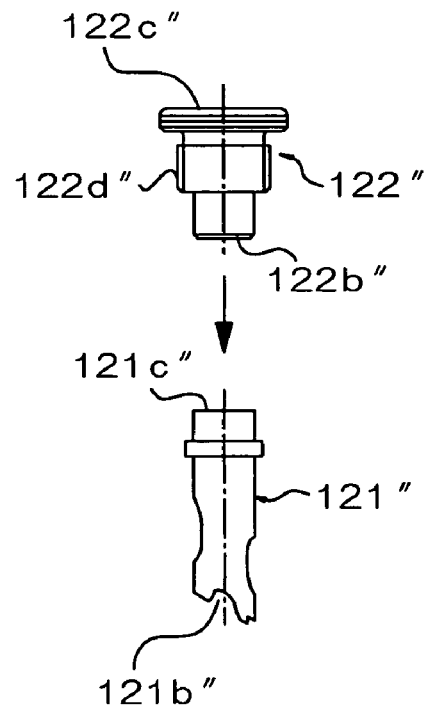
FIG. 6 is a side view of an engaging member and an adjusting member of another different constructional example.

FIG. 6 is a schematic explanatory view showing another constructional example of an engaging member 121" and an adjusting member 122", which are different from those of the above-described embodiment. Herein, although a retaining member 123 is unnecessary, other members are all the same in the construction as those of the above-described embodiment. In this constructional example, the adjusting member 122" has a male screw 122d" to be screwed into a male screw 118 formed in an axial hole of a nail body, and by a screwing amount thereof, a controlling position by an engaging portion 122b" is shifted in the axis direction. Here, a head portion 122c" has an enlarged form to be brought into contact against a rim portion of an opening 113a of a proximal end portion of the nail body 110. On the other hand, although the engaging member 121" has a distal-end engaging portion 121b" the same as that of the above-described embodiment, it is unnecessary to provide, on an contact engaging portion 121c" provided at its proximal end portion, a cam engaging surface the same as that of the above-described embodiment. Position of this engaging member 121" is controlled by merely a contact of the engaging portion 122b" of the adjusting member 122" against its contact engaging portion 121c".

In this constructional example, if the screwing amount of the adjusting member 122" is small, the controlling position of the engaging member 121" exists at a proximal-end-portion side of the nail body, and this is charged to the proximal-end-portion side by an elastic force of an elastic member 125 and is not engaged with a bone fastener. If the screwing amount of the adjusting member 122" is increased, since the controlling position of the engaging member 121" is shifted to a distal-end-portion side of the nail body, this is brought into a condition engaged with the bone fastener. In this constructional example, as long as the elastic force of the elastic member is applied to the proximal end side, no looseness in the screwed structure between the adjusting member 122" and nail body occurs, and accordingly, since the position of the engaging member 121" also does not jounce, the engaging member can be highly accurately engaged with the bone fastener. In this constructional example, a retaining member 123 the same as that of the above-described embodiment may be arranged so as to become a proximal-end-side stopper of (not the adjusting member) the engaging member 121" and the distal end of the adjusting member may be provided with a small diameter so that this distal end passes through the aperture inside of the retaining member 123 and reaches the engaging member 121".

FIG. 7A-7C and FIG. 8A, 8B illustrate detail structures of another tangible embodiment, which has the same essential structure as the constructional example illustrated in FIG. 6. In this embodiment, the same parts as the embodiment illustrated in FIG. 1-3 are referred with the same reference sign and explanations thereof are omitted. In this embodiment, although an engaging member 221, an adjusting member 222, and a retaining member 223 are different from the above intramedullary nail 100, and the others, for example, the nail body 110, the stopper member 124, and the elastic member 125 are constructed in the same fashion as the above. A bone fastener 10 is provided with engaging grooves 10b extending along the axis line at the outer circumferential surface thereof.

In this embodiment, as illustrated in FIGS. 7A and 7B, although the engaging member 221 is constructed in the similar fashion as the above engaging member 121" and is provided with an axial hole 221a, a distal-end engaging portion (corresponding to the above engaging member in the present invention) 221b, a transverse opening portion 221d and a concave groove 221e the same as those of the above engaging member 121, the engaging member 221 is not provided with a cam engaging portion and in place of it, has a contact engaging portion 221c with flat surface, which is constructed so as to be contacted with the adjusting member 222. The distal-end engaging portion 221b of the engaging member 221 is formed in a shape of projection so as to be able to insert into the engaging groove 10b on the bone fastener 10. However, this distal-end engaging portion 221b may be formed in the same shape as the distal-end engaging portion 121b of the engaging member 121.

The adjusting member 222 is comprising; a contact portion 222a to contact with the contact engaging portion 221c of the engaging member 221; a male screw 222b to be screwed into the female screw 118 equipped at the vicinity of the opening 113a of the axial hole 113; and a engaging structure 222c for a rotating operation. And the adjusting member 222 is provided with a shoulder portion 222d and this shoulder portion 222d is formed so as to be able to contact with the retaining member 223 in case that the downwardly sifting range of the engaging member 221 is adequately reserved.

The retaining member 223 is provided with an opening at the center thereof and the male screw at the outer circumferential surface thereof, basically the same as the retaining member 123. However, this embodiment is different from the above intramedullary nail 100 in that the retaining member 223 retains the engaging member 221 by the contact with the contact portion 221c of the engaging member 221 where screwing to the male screw 118. The adjusting member 222 is constructed so as to be able to contact with the contact portion 221c of the engaging member 221 through the opening of the retaining member 223 where screwing to the male screw 118. The elastic member 125 is stored between the proximal region 111 and the engaging member 221, and presses the engaging member 221 upwardly toward the proximal-end-portion side.

Figure 8A:
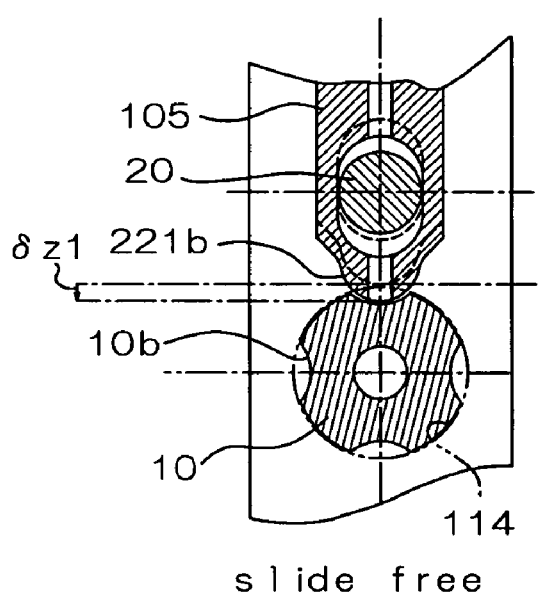
FIG. 8A is an enlarged sectional view of an engaging condition (slide-free condition) between the engaging member and a bone fastener.
Figure 8B:
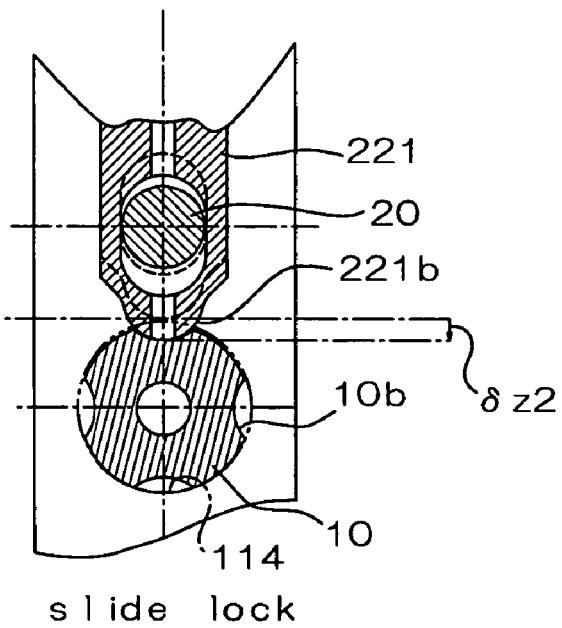
FIG. 8B is an enlarged sectional view of another engaging condition (slide-lock condition) between the engaging member and the bone fastener.

As illustrated in FIG. 7A, in a condition that the engaging member 221 and the elastic member 125 are inserted into the axial hole 113 of the nail body 110 and the retaining member 223 is retained in contact with the contact engaging portion 221c of the engaging member 221 where screwing to the male screw 118, by inserting the adjusting member 222 into the axial hole 113 and screwing it to the male screw 118, the contact portion 222a of the adjusting member 222 comes to contact with the contact engaging portion 221c of the engaging member 221. And after then, by screwing the adjusting member 222 more, the engaging member 221 is sifted downward against the elastic member 125. And then, as illustrated in FIG. 8A, finally the distal-end engaging portion 221b of the engaging member 221 protrudes downwardly into the transverse hole 114 by an amount of protrusion delta z1 and is inserted into the engaging groove 10b of the bone fastener 10, then makes the condition to prohibit the bone fastener 10 from the rotation around the axis line thereof (slide-free condition). And by further screwing the adjusting member 222, as illustrated in FIG. 8B, the distal-end engaging portion 221b of the engaging member 221 protrudes downwardly by an amount of protrusion delta z2 and strongly contacts with the bottom surface of the engaging groove 10b, then makes the condition to prohibit the bone fastener 10 from the slide in the axial direction (slide-lock condition). Here, the adjusting member 222 is provided with a distal protrusion 221t at the tip thereof, which is inserted into an axial hole 221a and positions the axis line of the engaging member 221.

On the contrary, as illustrated in FIG. 7B, it is preferable to prepare another adjusting member 222' formed with length from the contact portion 222a' to the shoulder portion 222d' shorter than that of the adjusting member 222. In the case of using this adjusting member 222', it becomes unable to press the engaging member 221 down any more when the shoulder portion 222d' of the adjusting member 222' contacts with the retaining member 223. Therefore, when the adjusting member 222' is screwed by maximum depth, as illustrated in FIG. 8A, the adjusting member 222 brings into the condition (slide-free condition) where the bone fastener is slidable in its axis direction but cannot rotate around its axis line. As stated above, use of a plurality of the adjusting member 222, 222' having different length from each other facilitates the adjusting operation.

In either of the embodiments, it is preferable that the engaging member has an engaging surface for the bone fastener, having a schematic surface form along the inner surface of the transverse hole and comprising an uneven engaging structure superposed on this schematic surface form. According thereto, since the engaging surface of the engaging member has a schematic surface form along the inner surface of the transverse hole, even when the shifting stroke of the engaging member is reduced, the engaging member is not projected inside the transverse hole before a bone fastener is inserted into the transverse hole. In addition, after the bone fastener is inserted through the transverse hole, owing to the engaging surface comprising a schematic surface form along the inner surface of the transverse hole, since an engaging surface area broader than that of the prior art can be secured, it becomes possible to more securely engage and retain the bone fastener. In particular, it is desirable that the schematic surface form is a surface form curved along the curved inner surface of the transverse hole and the uneven engaging structure of the engaging surface has unevenness when viewed in its curving direction.

In addition, it is preferable that, in the nail body, a plurality of transverse holes are formed so as to be arranged along the axis line, and the engaging member comprises, at a position corresponding to the transverse hole formed at a side of the proximal end portion of the nail body, a transverse opening portion through which another bone fastener to be inserted into the transverse hole formed at the side of the proximal end portion can be inserted. By providing the transverse opening portion in the engaging member, it becomes possible to insert, through the transverse hole formed closer to the proximal end side of the nail body than the transverse hole through which a bone fastener engaged and retained by the engaging member is inserted, another bone fastener and use the same.

Herein, an intramedullary nail of the present invention is not limited to only the foregoing illustrated examples, and as a matter of course, various modifications can be made without departing from the scope of the present invention. For example, although the adjusting member and engaging member of the above-described embodiment are separately constructed and retained in a mutually cam-engaged condition by the retaining member 123 and elastic member 125, the present invention is not limited to such a manner, and an adjusting member and an engaging member may be connected in a manner mutually rotatable and shiftable in the axis direction. At this time, an elastic member may be stored inside the connecting structure of the adjusting member and engaging member. In addition, although the distal-end engaging portion of the engaging member has a form coordinated with the inner surface of the transverse hole, the present invention is not limited to such a distal-end form and it can have a distal-end form of a projection form engaged with a groove of a bone fastener.

The entire disclosure of Japanese Patent Application No.2003-429252 filed on Dec. 25, 2003 including specification, claims, drawings and summary are incorporated herein by reference in its entirety.

What is claimed is:

1. An intramedullary nail for intramedullar insertion into a bone, having a nail body comprising an axial hole extending from an opening formed at a proximal end portion toward a distal end portion along an axis line and a transverse hole intersecting with the axis line, comprising:
    an engaging member comprising an engaging portion at distal end thereof engageable with a bone fastener inserted through the transverse hole and arranged so as to be shiftable in the axial hole such that the engaging portion is engageable and disengageable with the bone fastener;
    an adjusting member controlling the position of the engaging member from a side of the proximal end portion according to the operation thereof; and
    an elastic member for biasing the engaging member to the proximal end portion side in the axis direction against the nail body, and which is arranged between an outer circumferential step provided at the outer circumference of the engaging member and an inner step provided inside the axial hole of the nail body,
    whereby a first condition in which the engaging member engages with the bone fastener, by displacement of the engaging member to a side of the distal end portion in the axial direction against the biasing of the elastic member, and a second condition in which the engaging member does not engage with the bone fastener, by displacement of the engaging member to the side of the proximal end portion in the axial direction under the biasing of the elastic member, are selected by operation of the adjusting member.

2. The intramedullary nail as set forth in claim 1, further comprising a retaining member for retaining the engaging member from the side of the proximal end portion,
    the retaining member provided with an aperture in order to enable the adjusting member to contact with the engaging member from the side of the proximal end portion.

3. The intramedullary nail as set forth in claim 1, wherein the engaging member has an engaging surface for the bone fastener, having a schematic surface form along an inner surface of the transverse hole and comprising an uneven engaging structure superposed on this schematic surface form.

4. The intramedullary nail as set forth in claim 1, wherein in the nail body, a plurality of transverse holes are formed so as to be arranged along the axis line, and the engaging member comprises, at a position corresponding to the transverse hole formed at the side of the proximal end portion of the nail body, a transverse opening portion through which another bone fastener is inserted into the transverse hole formed at the side of the proximal end portion.

5. The intramedullary nail as set forth in claim 1, the adjusting member adapted for rotational operation and the adjusting member having a cam engagement with the engaging member so as to change a controlling position for the engaging member in accordance with the rotational angle of the adjusting member in a condition substantially fixed in the axial direction.

* * * * *

UNITED STATES PATENT AND TRADEMARK OFFICE
CERTIFICATE OF CORRECTION

PATENT NO. : 7,601,153 B2  Page 1 of 1
APPLICATION NO. : 11/018962
DATED : October 13, 2009
INVENTOR(S) : Shinjo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

Signed and Sealed this

Fifth Day of October, 2010

David J. Kappos
*Director of the United States Patent and Trademark Office*